United States Patent [19]

Becher et al.

[11] Patent Number: 5,607,977
[45] Date of Patent: Mar. 4, 1997

[54] BENZOYLUREAS

[75] Inventors: Heinz-Manfred Becher, Bingen am Rhein; Christo Drandarevski, Ingelheim am Rhein; Rudolf Mengel, Gau-Algesheim; Walter Ost, Bingen am Rhein, all of Germany

[73] Assignee: Shell Agrar GmbH & Co. KG, Ingelheim am Rhein, Germany

[21] Appl. No.: 780,457

[22] Filed: Oct. 22, 1991

Related U.S. Application Data

[63] Continuation of Ser. No. 597,272, Oct. 16, 1990, abandoned, which is a continuation of Ser. No. 430,917, Oct. 30, 1989, abandoned, which is a continuation of Ser. No. 260,458, Oct. 20, 1988, abandoned, which is a continuation of Ser. No. 76,266, Jul. 22, 1987, abandoned, which is a continuation of Ser. No. 900,430, Aug. 26, 1986, abandoned, which is a continuation of Ser. No. 780,045, Sep. 25, 1985, abandoned.

[30] Foreign Application Priority Data

Sep. 29, 1984 [DE] Germany .......................... 34 35 895.1
Mar. 14, 1985 [DE] Germany .......................... 35 09 075.8
Jul. 18, 1985 [DE] Germany .......................... 35 25 625.7

[51] Int. Cl.⁶ .......................... A01N 47/30; C07C 275/30
[52] U.S. Cl. .......................... 514/594; 564/44
[58] Field of Search .......................... 564/44; 514/594

[56] References Cited

U.S. PATENT DOCUMENTS

| | | | |
|---|---|---|---|
| 4,013,717 | 3/1977 | Wellings et al. | 564/44 |
| 4,310,548 | 1/1982 | Ehrenfreund et al. | 564/44 |
| 4,399,152 | 8/1983 | Brouwer et al. | 564/44 |
| 4,457,943 | 7/1984 | Becker et al. | 564/44 |
| 4,533,676 | 8/1985 | Sirrenberg et al. | 564/44 |
| 4,564,639 | 1/1986 | Nagase et al. | 564/44 |
| 4,622,340 | 11/1986 | Becker et al. | 564/44 |
| 4,711,905 | 12/1987 | Sirenberg et al. | 514/594 X |

FOREIGN PATENT DOCUMENTS

| | | | |
|---|---|---|---|
| 167557 | 9/1984 | Japan | 564/23 |
| 2106501 | 4/1983 | United Kingdom | 564/44 |
| 2106499 | 4/1983 | United Kingdom | 564/44 |

OTHER PUBLICATIONS

Chemical Abstracts 86:134880w (1977).
Chemical Abstracts 70:77561m (1969).
Chemical Abstracts 62:14546c (1965).
Chemical Abstracts, vol. 62, No. 12, Jun. 7, 1985, Abstract No. 14546c.
Chemical Abstracts, vol. 70, No. 17, Apr. 28, 1969, Abstract No. 77561m.
Journal of Agricultural and Food Chemistry, vol. 21, No. 3, 1973, pp. 348–354.
Chemical Abstracts, vol. 86, No. 19, May 9, 1977, Abstract No. 134880w.
Houben–Weyl, "Methoden der organischem Chemie", 4. Auflage, Band VIII: sauerstoffvergindunden III, 1952, Georg Thieme Verlag, Stuttgart, pp. 499, 680–684.
Houben–Weyl "Methoden der organischem Chemie", 4. Auflage, Band XI/1: stickstoffverbindungen II, 1957, Georg Thieme Verlag, Stuttgaft, p. 884.

*Primary Examiner*—Shailendra Kumar
*Attorney, Agent, or Firm*—Sughrue, Mion, Zinn, Macpeak & Seas

[57] ABSTRACT

Compounds of the formula

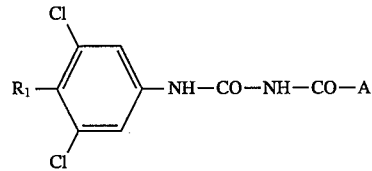

wherein $R_1$ is fluorine, chlorine, bromine or iodine; and
A is 2,6-difluorophenyl, 2-chlorophenyl, 2-chloro-6-fluorophenyl, 2,6-dichlorophenyl or 2-fluorophenyl,
with the proviso that when $R_1$ is chlorine, A is other than 2,6-dichlorophenyl, useful as pesticides.

2 Claims, No Drawings

BENZOYLUREAS

This is a continuation of application Ser. No. 07/597,272 filed Oct. 16, 1990, now abandoned, in turn a continuation of application Ser. No. 07/430,917 filed Oct. 30, 1989, abandoned; in turn a continuation of application Ser. No. 07/260,458 filed Oct. 20, 1988, abandoned; in turn a continuation of application Ser. No. 07/076,266 filed Jul. 22, 1987, abandoned; in turn a continuation of application Ser. No. 06/900,430 filed Aug. 26, 1986, abandoned; in turn a continuation of application Ser. No. 06/780,045 filed Sep. 25, 1985, abandoned.

This invention relates to novel benzoylureas, to methods of preparing these compounds, to insecticidal compositions containing them as active ingredients, and to a method of using them as insecticides.

BACKGROUND OF THE INVENTION

It is known from German Auslegeschrift No. 2,123,236 that certain benzoylureas exhibit insecticidal activity. These known compounds, however, are not always satisfactory with respect to efficacy, activity profile or toxicity.

OBJECTS OF THE INVENTION

It is an object of the present invention to provide novel benzoylureas which are significantly more effective insecticides than the prior art compounds.

Other objects and advantages of the present invention will become apparent as the description thereof proceeds.

DESCRIPTION OF THE INVENTION

More particularly, the present invention relates to a novel class of benzoylureas represented by the formula

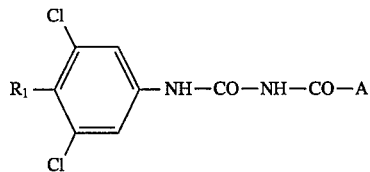

wherein $R_1$ is fluorine, chlorine, bromine or iodine; and
A is 2,6-difluorophenyl, 2-chlorophenyl, 2-chloro-6-fluorophenyl, 2,6-dichlorophenyl or 2-fluorophenyl,
with the proviso that when $R_1$ is chlorine, A is other than 2,6-dichlorophenyl.

Specific illustrative species of the class of compounds of the instant invention are the following:
N-(3,5-Dichloro-4-fluorophenyl)-N'-(2,6-difluorobenzoyl)-urea
N-(3,4,5-Trichlorophenyl)-N'-(2,6-difluorobenzoyl)-urea
N-(4-Bromo-3,5-dichlorophenyl)-N'-(2,6-difluorobenzoyl)-urea
N-(3,5-Dichloro-4-iodophenyl)-N'-(2,6-difluorobenzoyl)-urea
N-(3,5-Dichloro-4-fluorophenyl)-N'-(2-chlorobenzoyl)-urea
N-(3,4,5-Trichlorophenyl)-N'-(2-chlorobenzoyl)-urea
N-(4-Bromo-3,5-dichlorophenyl)-N'-(2-chlorobenzoyl)-urea
N-(3,5-Dichloro-4-iodophenyl)-N'-(2-chlorobenzoyl)-urea
N-(3,5-Dichloro-4-fluorophenyl)-N'-(2,6-dichlorobenzoyl)-urea
N-(4-Bromo-3,5-dichlorophenyl)-N'-(2,6-dichlorobenzoyl)-urea
N-(3,5-Dichloro-4-iodophenyl)-N'-(2,6-dichlorobenzoyl)-urea
N-(3,5-Dichloro-4-fluorophenyl)-N'-(2-chloro-6-fluorobenzoyl)-urea
N-(3,4,5-Trichlorophenyl)-N'-(2-chloro-6-fluorobenzoyl)-urea
N-(4-Bromo-3,5-dichlorophenyl)-N'-(2-chloro-6-fluorobenzoyl)-urea
N-(3,5-Dichloro-4-iodophenyl)-N'-(2-chloro-6-fluorobenzoyl)-urea
N-(3,5-Dichloro-4-fluorophenyl)-N'-(2-fluorobenzoyl)-urea
N-(3,4,5-Trichlorophenyl)-N'-(2-fluorobenzoyl)-urea
N-(4-Bromo-3,5-dichlorophenyl)-N'-(2-fluorobenzoyl)-urea and
N-(3,5-Dichloro-4-iodophenyl)-N'-(2-fluorobenzoyl)-urea The compounds embraced by formula I above may be prepared by the following methods which involve known chemical synthesis principles.

Method A

By reacting an aniline of the formula

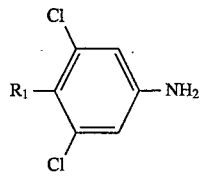

wherein $R_1$ has the meanings previously defined, with a benzoyl-isocyanate of the formula

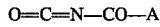

wherein A has the meanings previously defined.

Method B

By reacting a phenyl isocyanate of the formula

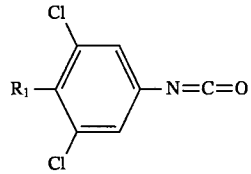

wherein $R_1$ has the meanings previously defined, with a benzamide of the formula

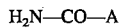

wherein A has the meanings previously defined.

Some of the starting compounds of the formulas II, III, IV and V are known.

Compounds of the formula II wherein $R_1$ is bromine or iodine, as well as compounds of the formula IV wherein $R_1$ is bromine or iodine are new. Thus, the present invention also relates to
4-Bromo-3,5-dichloro-aniline,
4-iodo-3,5-dichloro-aniline,
4-Bromo-3,5-dichloro-phenyl isocyanate, and
4-dichloro-3,5-dichloro-phenyl isocyanate.

The isocyanates of the formula IV may be prepared as follows:
  a) by reacting an aniline of the formula II with phosgene or a functional derivative thereof pursuant to known methods; or b) by the Curtius Rearrangement, starting from a reactive acid halide of the formula

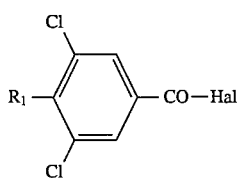
(VI)

wherein Hal is fluorine, chlorine, bromine or iodine, preferably chlorine or fluorine.

The acid halide of the formula VI is reacted in an inert solvent, preferably chlorobenzene, toluene or xylene, with an azide, preferably sodium azide or potassium azide, to form an acid azide of the formula

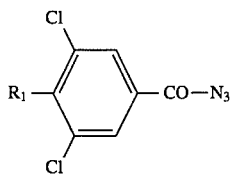
(VII)

If the reaction is performed at a temperature above about 100° C., the isocyanate of the formula IV can be isolated directly pursuant to the following reaction sequence.

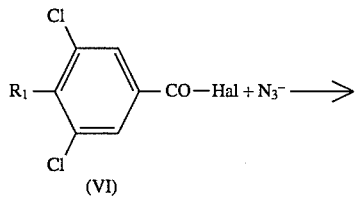

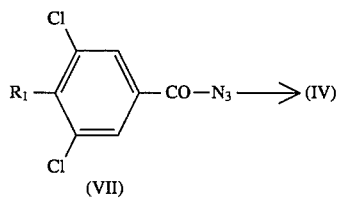

The reaction is preferably performed by adding the azide in portions to a solution of the acid halide which has been heated to a temperature above 100° C., whereby the azide of the formula VII which is formed in situ immediately further reacts accompanied by release of nitrogen, to form the isocyanate of the formula IV.

The azides of the formula VII may also be prepared by other methods described in the literature and may subsequently be subjected to a rearrangement into isocyanates of the formula IV, for instance, by reacting a 4-halo-3,5-dichloro-benzoyl hydrazide with a nitrite to form an azide of the formula VII.

The azide of the formula VII may, however, also be prepared initially at a lower temperature and may then be rearranged at a higher temperature into the isocyanate of the formula IV. Therefore, the present invention also relates to the following novel carboxylic acid azides of the formula VII:
3,5-dichloro-4-fluorobenzoic acid azide,
3,4,5-Trichloro-benzoic acid azide,
4-Bromo-3,5-dichloro-benzoic acid azide,
3,5-dichloro-4-iodo-benzoic acid azide.

It should be emphasized that 3,5-dichloro-4-fluoro-benzoic acid azide (formula VII, $R_1$=F) can be particularly advantageously prepared from readily available 3,4,5-trichloro-benzoyl chlorine (formula VI, $R_1$=Cl, Hal=Cl) by double halogen exchange.

In the case of the reaction of 3,4,5-trichloro-benzoyl chloride with a fluoride such as potassium fluoride, the chlorine atom in the 4-position of the aromatic system as well as the chlorine atom from the carboxylic acid function can be exchanged in a single reaction step. The 3,5-dichloro-4-fluorobenzoyl fluoride of the formula VI reacts under particularly mild conditions into the corresponding azide of the formula VII with good yields.

The anilines of the formula II can be prepared in a 2-step reaction sequence, starting from 2,6-dichloro-aniline of the formula VIII, where in the first reaction step the amino group is substituted pursuant to known methods by the halogens fluorine, chlorine, bromine or iodine, and the 4-halo-3,5-dichloro-nitrobenzene of the formula IX is reduced to the aniline of the formula II in the second reaction step pursuant to the following reaction sequence:

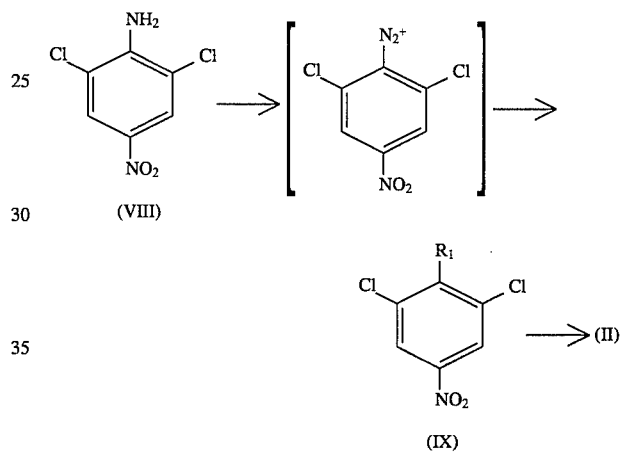

A benzoyl isocyanate of the formula III can be obtained from a corresponding benzoyl amide and oxalyl chloride.

The following examples illustrate the present invention and will enable others skilled in the art to understand it more completely. It should be understood, however, that the invention is not limited solely to the particular examples given below.

Preparation of Starting Compounds

EXAMPLE I

Preparation of 4,5-trichloro-phenyl isocyanate (IV) from 3,4,5-trichloro-aniline (II)

Hydrogen chloride gas was introduced at room temperature, accompanied by stirring, into a solution of 3,4,5-trichloro-aniline (29.6 g) in toluene (300 ml). Phosgene (30 g) was introduced into the resulting suspension of 3,4,5-trichloro-aniline hydrochloride, and the mixture was then heated at its boiling point until the reaction mixture became clear. In order to prevent the escape of phosgene it was necessary to use an intensive reflux cooler. After the reaction mixture turned virtually completely clear, the minor amount of residue was suction filtered off, the filtrate was evaporated and the oily isocyanate was isolated.

Yield: 32.1 g of the title compound in the form of an oil.

EXAMPLE 2

Preparation of 3,4,5-trichloro-phenyl isocyanate (IV) from 3,4,5-trichloro-benzoyl chloride (VI)

A solution of 3,4,5 trichloro-benzoyl chloride (24.4 g) in chlorobenzene (100 ml) was added dropwise, accompanied by stirring, to a solution of sodium azide (7.0 g) in chlorobenzene (300 ml) which had been heated to 125° C., whereby nitrogen was released. After all of the solution had been added and the evolution of nitrogen had subsided, the mixture was stirred for two hours more at 125° C. Thereafter, the reaction mixture was admixed with silica gel (3.0 g), and after cooling it was filtered at room temperature. After distilling off the solvent, the title compound was obtained in the form of an oil.

Yield: 22.1 g.

In place of chlorobenzene, toluene or xylene can also be used as the solvent and, if desired for the purpose of increasing the temperature, the reaction may also be performed at superatmospheric pressure.

EXAMPLE 3

Preparation of a 4-halo-3,5-dichloro-aniline (II) from 2,6-dichloro-4-nitroaniline (III) via a 4-halo-3,5-dichloro-nitrobenzene (IX)

A) Preparation of 3,4,5-trichloro-nitrobenzene (step 1)

Nitrosyl bisulfate (84.0 g) was added in small portions to a solution of 2,6-dichloro-4-nitroaniline (124.2 g) in a mixture of concentrated phosphoric acid (250 ml), glacial acetic acid (75 ml) and concentrated sulfuric acid (500 ml), said solution having been cooled to −5° C. Thereafter, the reaction mixture was stirred for one hour at 0° C., then for one hour at 5°–10° C., and finally for one hour at 15° C. A copper-(I)-chloride solution (0.80 mol) was added dropwise at 45° C., while vigorously stirring, to the resulting solution, and the mixture was stirred for one hour at 50°–60° C. The reaction mixture was then poured into ice (2 kg). After extraction with dichloro-methane, 3,4,5-trichloro-nitrobenzene was isolated.

Yield: 101 g (74% of theory); m.p. 68°–70° C.

A solution of 3,4,5-trichloro-nitrobenzene (34 g) in ethyl acetate (350 ml) was hydrogenated at room temperature and atmospheric pressure in the presence of 4.0 g Rainey nickel. After the uptake of hydrogen had ceased, the catalyst was separated by suction filtration and the filtrate was evaporated.

Yield: 25.7 g (87% of theory) of 3,4,5-trichloro-aniline (II), m.p. 97°–98° C.

B) Preparation of 4-bromo-3,5-dichloro-nitrobenzene (step 1)

This compound was prepared in analogy to (A) above by using a copper-(I)-bromide solution in place of the copper chloride solution.

Yield: 59% of theory of 4-bromo-3,5-dichloro-nitrobenzene (IX), m.p. 88°–90° C.

Preparation of 4-bromo-3,5-dichloro-aniline (step 2)

A solution of tin-(II)-chloride dihydrate (75.0 g) in concentrated hydrochloric acid (150 ml) was added dropwise to a boiling solution of 4-bromo-3,5-dichloro-nitrobenzene (27.1 g) in acetone (700 ml), while stirring, and the mixture was boiled for 30 minutes more. After distilling off the solvent, the reaction mixture was poured over ice, the aqueous mixture was made alkaline by addition of sodium hydroxide (10%), and the mixture was repeatedly extracted with ether. The combined ether extracts were evaporated, and the residue was purified with methylene chloride on a silica gel column.

Yield: 14.7 g (61% of theory) of 4-bromo-3,5-dichloro-aniline (II), m.p. 121°–123° C.

C) Preparation of 4-iodo-3,5-dichloro-nitrobenzene (step 1)

Sodium nitrite (12.0 g) was added in small portions, while stirring, to a solution of 2,6-dichloro-4-nitro-aniline (26.5 g) in concentrated sulfuric acid (200 ml). Thereafter, the reaction mixture was stirred for one hour more at 8°–10° C. and was then poured over ice (800 g). The aqueous mixture was admixed with an aqueous potassium iodide solution (30 g of a potassium iodide in 60 ml of water), which was accompanied by vigorous foaming. The mixture was then stirred for one hour more at room temperature, extracted with ether, the combined ether extracts were evaporated, and the residue was purified with dichloro-methane on a silica gel column.

Yield: 25.0 g (58% of theory) of 4-iodo-3,5-dichloro-nitrobenzene, m.p. 153°–158° C.

Preparation of 4-iodo-3,5-dichloro-aniline (step 2)

Using a procedure analogous to that described in (B) above, 4-iodo-3,5-dichloro-aniline, m.p. 147°–148° C., was obtained with an 85% yield, starting from 4-iodo-3,5-dichloro-nitrobenzene.

Preparation of end products of the formula I

Synthesis of benzoylureas of the formula I, starting from 4-halo-3,5-dichloro-aniline and a benzoyl isocyanate of the formula III.

EXAMPLE 4

Preparation of N-(3,4,5-trichloro-phenyl)-N'-(2,6-difluorobenzoyl)-urea 3,4,5-trichloro-aniline (19.7 g) and 2,6-difluorobenzoyl isocyanate (18.3 g) were dissolved in toluene (200 ml) at 50° C., and the solution was allowed to stand at this temperature for five hours. After cooling the solution to room temperature, the title compound was isolated by suction filtration and dried.

Yield: 34.2 g (90% of theory) as a crystalline compound, m.p. 231°–232° C.

Using a procedure analogous to that described in Example 4 the following compounds of the formula

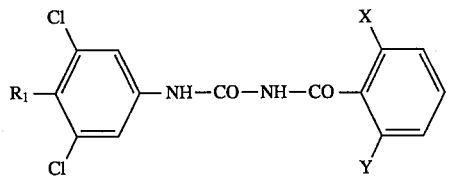

listed in Table I below were also prepared.

TABLE I

| Example No. | $R_1$ | X | Y | m.p./°C./ |
|---|---|---|---|---|
| 5 | F | F | F | 209–212° |
| 6 | Cl | Cl | Cl | 248–251° |
| 7 | Cl | H | Cl | 253–255° |
| 8 | Br | F | F | 230–233° |
| 9 | Br | F | Cl | 240–242° |
| 10 | Br | H | Cl | 243–245° |
| 11 | I | F | F | 243–245° |
| 12 | I | F | Cl | 245–247° |
| 13 | I | H | Cl | 257–259° |

TABLE I-continued

| Example No. | R₁ | X | Y | m.p./°C./ |
|---|---|---|---|---|
| 14 | F | Cl | Cl | |
| 15 | Br | Cl | Cl | |
| 16 | I | Cl | Cl | |
| 17 | F | H | Cl | |
| 18 | F | Cl | F | |
| 19 | F | H | F | |
| 20 | Cl | H | F | |
| 21 | Br | H | F | |
| 22 | I | H | F | |

Synthesis of benzoylureas of the formula I starting from a 4-halo-3,5-dichloro-phenyl isocyanate and a benzamide of the formula V.

EXAMPLE 23

Preparation of N-(3,4,5-trichloro-phenyl)-N'-(2,6-difluorobenzoyl)-urea

A solution of 3,4,5-trichloro-phenyl isocyanate (22.3 g), 2,6-difluoro-benzamide (15.7 g) in toluene (200 ml) was heated for eight hours at 90°–95° C. The title compound slowly crystallized out of the initially clear solution and was isolated by suction filtration after cooling of the reaction mixture.

Yield: 34.5 g (90% of theory), m.p. 231°–232° C.

Using a procedure analogous to that described in Example 23, the following compounds of the formula

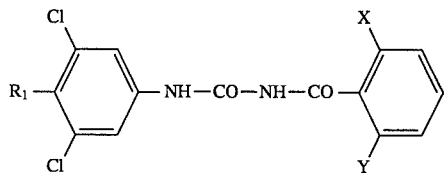

listed in Table II below were also prepared.

TABLE II

| Example No. | R₁ | X | Y | m.p./°C./ |
|---|---|---|---|---|
| 24 | F | F | F | 209–212° |
| 25 | Cl | F | Cl | 248–251° |
| 26 | Cl | H | Cl | 253–255° |
| 27 | Br | F | F | 230–233° |
| 28 | Br | F | Cl | 240–242° |
| 29 | Br | H | Cl | 243–245° |
| 30 | I | F | F | 243–245° |
| 31 | I | F | Cl | 245–247° |
| 32 | I | H | Cl | 257–259° |
| 33 | F | Cl | Cl | |
| 34 | Br | Cl | Cl | |
| 35 | I | Cl | Cl | |
| 36 | F | H | Cl | |
| 37 | F | Cl | F | |
| 38 | F | H | F | |
| 39 | Cl | H | F | |
| 40 | Br | H | F | |
| 41 | I | H | F | |

The compounds embraced by formula I above have useful properties. More particularly, they exhibit pesticidal activity against insects, spiders and nematodes. They are therefore useful as pesticides in the hygiene, food and veterinary sectors. The compounds are especially effective against pests in the development stage during which skin shedding takes place (chitin synthesis inhibition).

Insect pests against which the compounds of the instant invention are effective include the following:

From the order of Lepidoptera, for example:

*Plutella maculipennis, Leucoptera coffeella, Hypono meuta malinellus*, argyresthia conjugella, *Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspevresia molesta, Laspeyresia funebrana, Ostrinia nubilalis, Loxostege sticticalis, Ephestia kuehniella, Chilo suppressalis*, Galleria Mellonella, *Malacosoma neustria, Dendrolimus pini, Thaumatopoea pityocampa, Phalera bucephala, Cheimatobia brumata, Hibernis defoliaria, Bupalus piniarus, Hypnantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar, Lymantria monacha, Pieris brassicae, Aporia crataegi, Pectinophora gossypielle, Heliothis virescens;*

From the order of Coleoptera, for example:

*Epilachna varivestris, Phyllopertha horticola, Crioceris asparagi, Lemma melanopus, Leptinotarsa decemlineata, Diabrotica 12-punctata, Anthonomus grandis, Sitophilus granaria;*

From the order of Diptera, for example:

*Phagoletis cerasi, Rhagoletis pomonella, Anopheles maculipennis, Culex piplens, Aedes aegypti, Aedes vexans, Musca domestica, Fannia canicularis, Muscina stabulans, Glossina morsitans, Lucilia cuprina, Lucilia sericata, Hypoderma lineata;*

From the order of Hymenoptera, for example:

*Cephalcia abietis, Diption pini, Diprion sertifer, Pristiphora abietina,* pests from the order of Heteroptera,

From the order of Homoptera, for example:

*Bemisia tabaci, Psylla piri, Trialeurodes vaporariorum.*

The class of Arachnoidea includes spiders (Acarina), for example *Phyllocptrnta oleivora.*

The compounds of formula I may also be used to combat snails, land-living slugs and snails.

Examples of slugs include *Arion rufus, Arton ater* and other Ariontdae, varieties of Ltmax and the field slugs such as *Deroceras reticulatum* and *D. agreste* from the Milacidae family.

They are also harmful to snails, e.g. those of the genera Bradybaena, Cepaea, Cochlodina, Discus, Euomphalia, Galba, Helicigona, Helix, Helicella, Helicodiscus, Lymnaea, Opeas, Vallonia and Zonitoides.

For pesticidal purposes, the compounds of the formula I above may be used as such or as active ingredients in conventional pesticidal compositions, that is, compositions consisting essentially of an inert carrier and an effective pesticidal amount of the active ingredient, such as solutions, powders, suspensions, dispersions, emulsions, oil dispersions, pastes, dusting compositions or granulates which are disseminated by spraying, atomizing, dusting, scattering or watering. The particular type of composition depends upon the purpose of use; which should in any case provide for the fine distribution of the active ingredient according to the present invention.

As inert carriers for the preparation of sprayable solutions, emulsions, pastes or oil dispersions, mineral oil fractions of medium to high boiling point, such as kerosene or diesel oil; as well as coal tar oils and oils of vegetable or animal origin;

aliphatic, cyclic and aromatic hydrocarbons such as benzene, toluene, xylene, paraffin, tetrohydranaphthalene, alkylated naphthalenes or their derivatives, such as methanol, ethanol, propanol, butanol, chlorform, carbontetrachloride, cyclohexanol, cyclohexanone, chlorobenzene, isophorn; strong polar solvents such as dimethylformamide, dimethylsulfoxide, N-methylpyrrolidone, or water may be used.

Aqueous compositions may be prepared from emulsion concentrates, suspension concentrates, pastes or wettable powders (spray powders, oil dispersions) by addition of water. For the preparation of emulsions, pastes or oil dispersions, the active ingredients of the instant invention may be homogenized in water as such or in solution in an oil or solvent by means of wetting, adhesion, dispersing or emulsifying agents. Similarly, concentrates consisting of active ingredients, wetting, adhesion, dispersing or emulsifying agents, optionally also containing solvents or oil, which are suitable for dilution with water, can be prepared.

Suitable surfactive or wetting agents include alkali metal, alkaline earth metal, or ammonium salts of lignin sulfonic acid, naphthalene sulfonic acid or phenyl sulfonic acid, alkylarylsulfonates, alkylsulfates, alkylsulfonates, alkali metal and alkaline earth metal salts of dibutylnaphthalene sulfonic acid, laurylether sulfate, fatty alcohol sulfates, fatty acid alkali metal and alkaline earth metal salts, salts of sulfated hexadecanols, heptadecanols or octadecanols, salts of sulfated fatty alcohol glycol ether, condensation products of sulfonated naphthalene and naphthalene derivatives with formaldehyde, condensation products of naphthalene or naphthalene sulfonic acids with phenol and formaldehyde, polyoxyethylene-octylphenolether, ethoxylated isooctylphenol, octylphenol, nonylphenol, alkylphenol polygylcolether, tributylphenyl polygylcolether, alkylaryl polyether alcohol, isotridecyl alcohol, fatty alcohol-ethylene oxide condensates, ethoxylated castor oil, polyoxyethylene-alkylether, ethoxylated polyoxypropylene, lauryl alcohol polygylcolether acetal, sorbitol esters, lignin, sulfite waste liquors and methyl cellulose.

For pesticidal application the active ingredients according to the invention are processed with conventional excipients and/or carriers into conventional compositions, such as emulsion concentrates, suspension powders, suspension concentrates or dusting powders. The active ingredients are disseminated in the form of sprays or dusting compositions with an active ingredient concentration between about 0.0005 and 2 percent or in the form of ultra-low-volume composition with higher active ingredient concentrations (up to about 90 percent). The effective amount of active ingredient is between about 0.005 and 0.5 kg per hectare, preferably 0.01 and 0.25 kg per hectare.

The following example illustrates a pesticidal composition comprising a compound of the present invention as an active ingredient and represents the best mode contemplated of using the invention.

EXAMPLE 42

Wettable powder

25% by weight of N-(3,5-dichloro-4-fluorophenyl)-N'-(2, 6-difluorobenzoyl)-urea

55% by weight of kalolin

10% by weight of colloidal silicic acid

9% by weight of lignin sulfonate (dispersing agent)

1% by weight of sodium tetrapropylene benzene sulfonate (wetting agent).

The ingredients are processed in conventional manner into a wettable powder (particle size: 4μ). Prior to use, a spray containing about 0.0005 to 0.5 weight percent of active ingredient is prepared by dilution with water.

Any one of the other compounds embraced by formula I may be substituted for the active ingredient in Example 42, and the amount of active ingredient or the amount and nature of the excipients may be varied to meet particular requirements.

While the invention has been illustrated with the aid of certain specific embodiments thereof, it should be understood that the invention is not limited thereto, and that various modifications and changes may be made without departing from the spirit of the invention or the scope of the appended claims.

We claim:

1. N-(3,4,5-trichlorophenyl)-N'-(2,6-difluorobenzoyl)-urea.

2. A pesticidal composition consisting essentially of an inert carrier and an effective pesticidal amount of the compound of claim 1.

* * * * *